(12) United States Patent
Zhao et al.

(10) Patent No.: US 11,160,439 B2
(45) Date of Patent: Nov. 2, 2021

(54) OPTICAL SYSTEM AND A SURGICAL INSTRUMENT WITH SUCH AN OPTICAL SYSTEM

(71) Applicant: OLYMPUS Winter & Ibe GmbH, Hamburg (DE)

(72) Inventors: Jianxin Zhao, Hamburg (DE); Mario Bock, Hamburg (DE)

(73) Assignee: OLYMPUS Winter & Ibe GmbH, Hamburg (DE)

(*) Notice: Subject to any disclaimer, the term of this patent is extended or adjusted under 35 U.S.C. 154(b) by 0 days.

(21) Appl. No.: 16/561,719

(22) Filed: Sep. 5, 2019

(65) Prior Publication Data

US 2020/0000321 A1  Jan. 2, 2020

Related U.S. Application Data

(62) Division of application No. 15/662,378, filed on Jul. 28, 2017, now Pat. No. 10,441,138.

(30) Foreign Application Priority Data

Jul. 29, 2016 (DE) .......................... 102016214025.6

(51) Int. Cl.
*G02B 5/04* (2006.01)
*A61B 1/00* (2006.01)
(Continued)

(52) U.S. Cl.
CPC ...... *A61B 1/00096* (2013.01); *A61B 1/00195* (2013.01); *A61B 1/042* (2013.01);
(Continued)

(58) Field of Classification Search
CPC . A61B 1/00096; A61B 1/00195; A61B 1/042; A61B 1/313; G02B 23/2423;
(Continued)

(56) References Cited

U.S. PATENT DOCUMENTS 2,678,580 A * 5/1954 Erban ...................... G02B 5/04
359/735
4,138,192 A  2/1979 Yamasita
(Continued)

FOREIGN PATENT DOCUMENTS

DE  10 2010 022 430 A1  12/2011
DE  10 2014 211 367 A1  12/2015
(Continued)

OTHER PUBLICATIONS

Japanese Notification of Reasons for Refusal dated Sep. 25, 2018 received in Japanese Patent Application No. 2017-144573, together with an English-language translation.
(Continued)

*Primary Examiner* — Thong Q Nguyen
(74) *Attorney, Agent, or Firm* — Scully, Scott, Murphy & Presser, P.C.

(57) ABSTRACT

An optical system including: a distal optical assembly; a proximal optical assembly; and an image sensor; wherein the distal and proximal optical assemblies define a beam path; the distal optical assembly couples incident beams of light from a field of view located in an object space in the proximal optical assembly; the proximal optical assembly directs the incident beams of light onto a light-sensitive surface of the image sensor; and at least one of the distal and proximal optical assemblies comprise, at least one prism arranged in the beam path, such that the at least one prism limits the field of view of the optical system on at least one side.

6 Claims, 3 Drawing Sheets

(51) Int. Cl.
  *G02B 23/24* (2006.01)
  *G02B 13/00* (2006.01)
  *A61B 1/04* (2006.01)
  *A61B 1/313* (2006.01)
(52) U.S. Cl.
  CPC .............. *A61B 1/313* (2013.01); *G02B 5/04* (2013.01); *G02B 13/00* (2013.01); *G02B 23/2423* (2013.01); *G02B 23/2446* (2013.01)
(58) Field of Classification Search
  CPC .... G02B 23/2446; G02B 23/00; G02B 23/02; G02B 23/2407; G02B 5/04; G02B 27/0018; G02B 5/00
  USPC .................. 359/831–837, 431–435, 613
  See application file for complete search history.

(56) References Cited

U.S. PATENT DOCUMENTS

| | | | | |
|---|---|---|---|---|
| 4,140,364 | A * | 2/1979 | Yamashita | A61B 1/00165 359/367 |
| 4,783,156 | A * | 11/1988 | Yokota | G02B 17/02 359/736 |
| 4,815,833 | A | 3/1989 | Zobel et al. | |
| 4,969,708 | A * | 11/1990 | Leiner | A61B 1/00165 385/117 |
| 5,377,047 | A | 12/1994 | Broome et al. | |
| 5,835,276 | A * | 11/1998 | Asai | G02B 27/0018 359/638 |
| 6,178,042 | B1 | 1/2001 | Imamura | |
| 6,659,942 | B2 * | 12/2003 | Lederer | G02B 23/2423 359/833 |
| 7,350,928 | B2 * | 4/2008 | Liao | G03B 21/28 348/759 |
| 8,072,483 | B2 | 12/2011 | Tomioka | |
| 9,625,700 | B2 | 4/2017 | Dahmen | |
| 2001/0036754 | A1 | 11/2001 | Maeda et al. | |
| 2008/0074624 | A1 * | 3/2008 | Liu | G02B 5/04 353/81 |
| 2010/0238666 | A1 * | 9/2010 | Ominato | F21V 5/02 362/308 |
| 2012/0035422 | A1 | 2/2012 | Lei et al. | |
| 2014/0092482 | A1 * | 4/2014 | Dubroca | G02B 27/0101 359/633 |
| 2014/0211321 | A1 * | 7/2014 | Sugihara | G02B 27/0172 359/631 |

FOREIGN PATENT DOCUMENTS

| | | |
|---|---|---|
| JP | 62-179716 U | 11/1987 |
| JP | 2000-98263 A | 4/2000 |

OTHER PUBLICATIONS

U.S. non-Final Office Action dated Mar. 22, 2019 issued in corresponding U.S. Appl. No. 15/662,378.

U.S. Final Office Action dated Oct. 25, 2018 issued in corresponding U.S. Appl. No. 15/662,378.

U.S. non-Final Office Action dated Jul. 19, 2018 issued in corresponding U.S. Appl. No. 15/662,378.

* cited by examiner

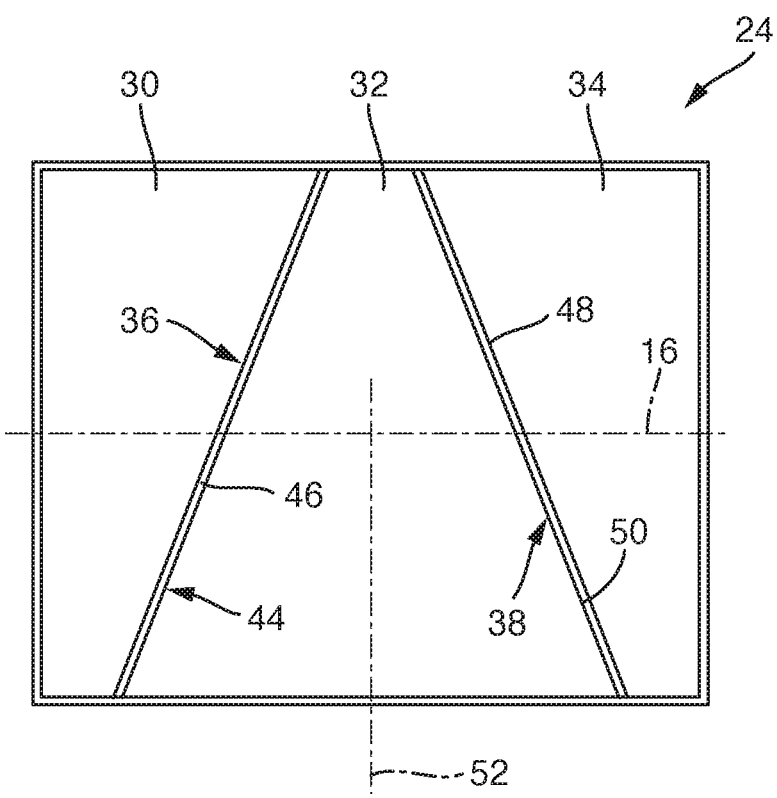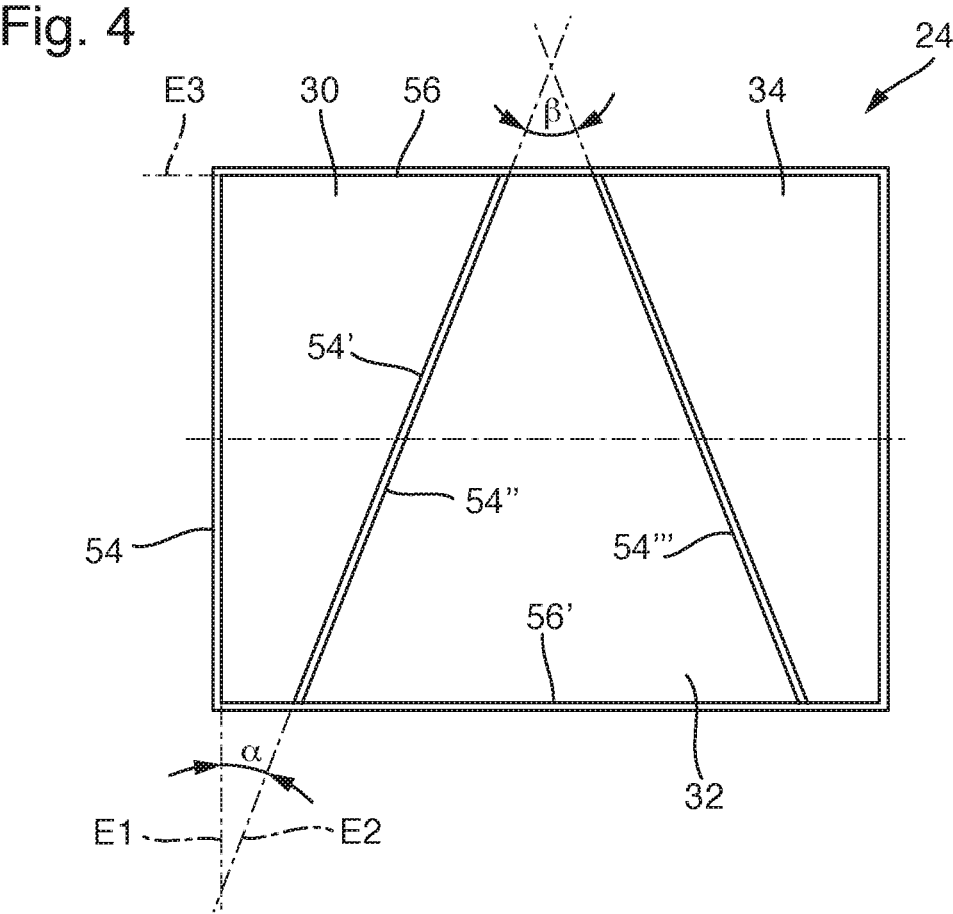

OPTICAL SYSTEM AND A SURGICAL INSTRUMENT WITH SUCH AN OPTICAL SYSTEM

CROSS-REFERENCE TO RELATED APPLICATIONS

This application is a Divisional application of U.S. Ser. No. 15/662,378 filed Jul. 28, 2017, which claims the benefit to DE 10 2016 214 025.6 filed on Jul. 29, 2016, the entire contents of which is incorporated herein by reference.

BACKGROUND

Field

The present application concerns an optical system comprising a distal optical assembly, a proximal optical assembly and an image sensor, wherein the distal and proximal optical assemblies define a beam path, and the distal optical assembly couples incident beams of light from a field of view located in an object space in the proximal optical assembly, and the proximal optical assembly directs these beams of light onto a light-sensitive surface of the image sensor. The present application also concerns a surgical instrument with such an optical system.

Prior Art

The optical elements of an optical system, generally one or more lenses, map incident beams of light from a field of view onto a light-sensitive surface of an image sensor. These beams of light occur within a beam path defined by the optical assemblies of the optical system, more precisely by their optical elements.

The field of view of the optical system refers to an area or an interval of viewing angles within which events or changes in the object space can be perceived with the optical system. Incident beams of light from the field of view are mapped on the light-sensitive surface of the image sensor. With a rectangular image sensor, the field of view is defined by a horizontal viewing angle and by a vertical viewing angle. The horizontal and vertical viewing angles are limited by the edges of the imaging format, which in turn depends on the size and shape of the image sensor. With a rectangular image sensor, the vertical viewing angle is typically smaller than the horizontal viewing angle (landscape format). The horizontal viewing angle and the vertical viewing angle are thus the maximum possible angles of incidence below which beams of light can enter the optical system and still be mapped on the light-sensitive surface of the image sensor.

If beams of light enter the optical system with larger angles, reflections occur at the optical elements. These beams of light also cause diffuse scattering or reflection on a tube or lens tube in which the optical elements of the optical system are received. These reflections, also often referred to as "flare" or "lens flare", adversely affect the image quality of the optical system.

Traditionally, the entry of such beams of light is reduced by mechanical masks or apertures in the optical system. However, masks or apertures often lead to strong vignetting, i.e. shading up to the edge of the image. Such masks also require very tight manufacturing tolerances for the optical system.

FIG. 1 shows an optical system 2 according to prior art in a schematically simplified longitudinal section view. Incident beams of light 6 (of which only one bears a reference label for reasons of clarity) from an object space 4 first fall upon an entry window 8. The optical system 2 is, for example, a component of a surgical instrument, furthermore the optical system 2 of an endoscope, for example. Within an endoscope, the entry window 8 hermetically seals the interior space of an endoscope at its distal end with respect to an exterior space or object space 4. If the beams of light 6 have passed through the entry window 8, they encounter a distal optical assembly 10 and afterward reach a proximal optical assembly 12. The distal and proximal optical assemblies 10, 12 define a beam path 14 in the optical system 2.

A field of view 20 is situated in the object space 4, which is defined by a horizontal and a vertical viewing angle. The longitudinal section shown in FIG. 1 shows a section along a vertical plane, for example. Consequently, the vertical viewing angle is to be seen. It is the angle between an optical axis 16 of the optical system 2 and the light beam 6 which just strikes a light-sensitive surface 19 of an image sensor 18. The field of view 20 is suggested schematically in FIG. 1 with an arrow. The distal optical assembly 10 and the proximal optical assembly 12 image incident beams of light 6, 6' from the field of view 20 on the light-sensitive surface 19 of the image sensor 18.

If, however, beams of light 6" from outside of the field of view 20 enter the optical system 2, these cause diffuse scattering and reflections in the optical system 2. For example, diffuse scattering occurs on an interior wall of a tube or of a lens tube of the optical system 2. This is suggested in FIG. 1 with star shaped markings which are intended to indicate scattering centers 22. These reflections or scatterings cause "flare" or "lens flare", a phenomenon which adversely affects the image quality of the optical system 2.

FIG. 5 shows another optical system 2 according to prior art. The optical system 2 is used, for example, in a stereo video endoscope with a lateral line of vision. It is located in the endoscope behind an entry window 8 through which beams of light 6 enter from the field of view 20 into the optical system 2. The beams of light 6 first of all enter the distal optical assembly 10, which includes an entry lens 26, a deflecting prism group 58 and an exit lens 28. A proximal optical assembly 12 of the optical system 2 shown includes a left and right lens system channel. Only the left lens system channel 60 is shown as an example in FIG. 5. A left image sensor 18L is located in the left lens system channel 60. Incident beams of light 6 entering the optical system 2 from the field of view 20 are imaged on the left image sensor 18L and a right image sensor, not shown, by the distal optical assembly 10 and by the proximal optical assembly 12 in a beam path 14. An incident light beam 6" from outside the field of view 20 causes a ghost image in the optical system 2 by multiple reflection. The light beam is reflected twice on a back side 57 and twice on a front side 59 of a second deflecting prism 61 of the deflecting prism group 58.

SUMMARY

It is an object to provide an improved optical system and an improved surgical instrument with such an optical system, wherein the optical system is to be particularly insensitive to incident beams of light outside a field of view.

Such object can be solved by an optical system comprising a distal optical assembly, a proximal optical assembly and an image sensor, wherein the distal and proximal optical assemblies defines a beam path, and the distal optical assembly couples incident beams of light from a field of view located in an object space in the proximal optical assembly, and the proximal optical assembly directs these beams of light onto a light-sensitive surface of the image sensor, wherein the optical system is developed by a group of prisms arranged in the beam path, with at least one prism, and wherein the prism group limits the field of view of the optical system on at least one side.

Thus according to another exemplary embodiment, the proximal optical assembly can comprises a left lens system channel with a left optical axis and a right lens system channel with a right optical axis. The left and right lens system channels can be configured similarly, and the left and right optical axes can be oriented parallel with respect to one another. The distal optical assembly can be configured so that the incident light from the object space is to be coupled to both the left lens system channel and the right lens system channel of the proximal optical assembly.

Such an optical system can be uses in a stereo video endoscope.

The object can be further solved by a surgical instrument, such as an endoscope or a stereo video endoscope, with an optical system according to one or more of the previously described embodiments.

The optical system can be the optical system of a surgical instrument, such as the optical system of a stereo video endoscope.

The same or similar advantages apply to the surgical instrument, such as to the endoscope, as were already mentioned with respect to the optical system itself. An optical system with high insensitivity to light scattering can be specified, which is furthermore efficient and simple to manufacture.

Further characteristics will be apparent from the description of embodiments together with the claims and the drawings included. Inventive embodiments can meet individual characteristics or a combination of several characteristics.

BRIEF DESCRIPTION OF THE DRAWINGS

The embodiments are described below, without restricting the general concept, based on exemplary embodiments with reference to the drawings; we expressly refer to the drawings with regard to the disclosure of all details that are not explained in greater detail in the text. In the figures:

FIG. 3 illustrates a prism group of the optical system from FIG. 2 in a schematically simplified longitudinal section;

FIG. 4 illustrates a further representation of the prism group from FIG. 3 in a schematically simplified longitudinal section;

In the drawings, the same or similar types of elements or parts are provided with the same reference numbers in order to avoid the need for redundant presentation in each case.

DETAILED DESCRIPTION

Figure 1:
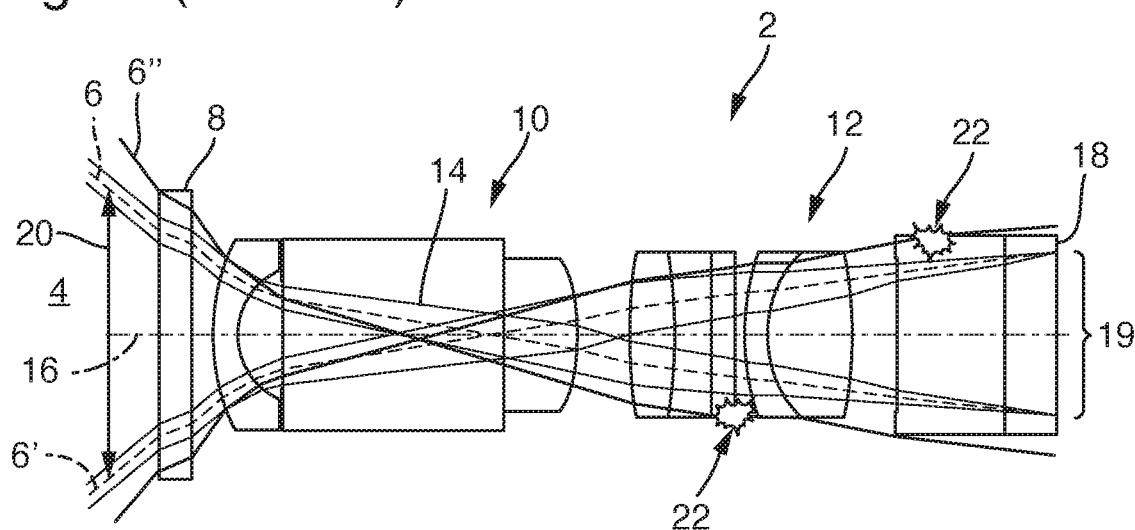
FIG. 1 illustrates an optical system according to prior art, in a schematically simplified longitudinal section.

The prism group can provide an angle-dependent optical filter with which incident beams of light entering the optical system from outside the field of view are reflected out of the beam path. No vignetting occurs and there are also no particularly strict requirements for centering or adjustment of the prism group in the optical system. Furthermore, a prism group is inexpensive to manufacture and can be integrated in the optical system without great design effort.

The prism group can be incorporated in the optical system in a manner able to rotate. For example, the prism group in the optical system can be rotatable on one axis which at least approximately corresponds to the optical axis of the optical system, such as, an optical axis of the distal optical assembly of the optical system. Rotation of the prism group can limit the field of view in a variable manner on different sides with the aid of the prism group.

According to another embodiment, the at least one prism can include a boundary surface at which incident beams of light from outside the field of view are reflected out of the beam path with total reflection. This boundary surface can be a boundary surface of an optically denser medium with an optically less dense medium. For example, it can be a glass/air boundary surface.

The beams of light reflected out can enter the distal optical assembly on one side of the field of view, at which the prism group of the field of view is limited.

The prism group which makes use of the total reflection at one boundary surface according to a further embodiment can be provided, in that the prism group comprises at least a first and a second prism, wherein the first prism comprises the boundary surface at which total reflection occurs and the second prism is arranged abutting this boundary surface, wherein a first air gap is present between the first prism and the second prism.

Thus, the first prism and the second prism can be arranged directly adjacent to one another. As an alternative to an air gap between the first prism and the second prism, a connection of the two prisms can be provided at the boundary surface at which total reflection takes place, wherein a material can be used to connect the two prisms, which has lower optical density than the material of the first prism.

Total reflection takes place when light strikes a boundary surface which lies between an optically denser medium and an optically less dense medium. In this process, the totally reflected light strikes the boundary surface at an angle which is greater than the critical angle for the given pair of materials. The angles are observed with reference to a vertical perpendicular at the boundary surface. The totally reflected beam always expands in the optically denser medium. A glass/air boundary surface represents a very simple possibility for providing this situation in which a beam of light is totally reflected.

According to another embodiment, the prism group can also include a third prism, wherein the first to third prism can be configured to have mirror symmetry with respect to a vertical plane perpendicular to an optical axis of the prism group.

A mirror-symmetric system can comprise a prism group, which includes in the direction of incident light, a first rectangular prism as a first prism, and an isosceles prism as a second prism, and a second rectangular prism as a third prism one after another. The second prism can comprise a second boundary surface at which total reflection takes place. The third prism can be arranged abutting this second boundary surface, wherein a second air gap can be present between the second prism and the third prism.

Also, instead of the second air gap, a material can be provided which has a lower optical density than the material of the second prism.

The field of view can be limited on two sides by reflection on the first and the second boundary surface. In accordance with further exemplary embodiments, it is possible by adding additional prisms to limit the field of view on further sides as well.

It is particularly provided that the first and second boundary surface are inclined in different directions, so that the beams of light reflected out of the beam path leave the beam path in directions which are also different.

Here the first and second boundary surface can be inclined about a first and a second axis. The first and second axes lie at least approximately parallel with respect to one another or have directions perpendicular to one another. The boundary surfaces at which total reflection takes place are, for example, oriented parallel to the sides of the isosceles prism which acts as a second prison. Here the first boundary surface is provided by a surface of the first prism, while the second boundary surface is provided by a surface of the second prism.

According to another embodiment, the at least one prism of the prism group can be a straight prism. The at least one prism can comprise two optically effective prism surfaces which enclose an acute angle and an optically non-effective surface opposite to the acute angle. A first plane in which a first optically effective prism surface lies, a second plane in which a second optically effective prism surface lies, and a third plane in which the surface lies together enclose a triangle which is a base surface of the prism at least in an area.

Thus, in other words, the first through third plane can enclose the tris angle. An optically effective boundary surface is understood to be a boundary surface which lies in the beam path. The base area of the prism is not necessarily triangular. For example, it could be a wedge or a triangle with a truncated tip.

According to a further embodiment, the prism group can comprise at least a first prism and a second prism, wherein the first and second prisms are arranged such that a first acute angle of the first prism and a second acute angle of the second prism lie on mutually opposing sides of the prism group.

In other words, the first acute angle and the second acute angle are, thus not opened in a mutually opposing direction.

The first and second prisms can be arranged one after another in the direction of incident light, wherein the first prism can be a rectangular prism. This embodiment of the prism group is simple to implement and at the same time very efficient optically.

Another embodiment is that the prism group can be a part of the distal optical assembly, wherein the distal optical assembly can comprise an entry lens and the prism group is arranged directly after the entry lens in the direction of incident light.

This arrangement of the prism group can provide incident beams of light from outside the field of view which cause light scattering effects in the optical system that are already removed from the beam path at the beginning of the optical system. This can contribute significantly to improving image quality of the optical system.

Furthermore, the proximal optical assembly is not influenced at all by the measures taken to improve the image quality. Thus, the optical system is very flexible with respect to the design of the proximal optical assembly.

The optical system can comprise at least one image sensor. Furthermore, the optical system can be an optical system for recording stereoscopic image data.

Figure 2:
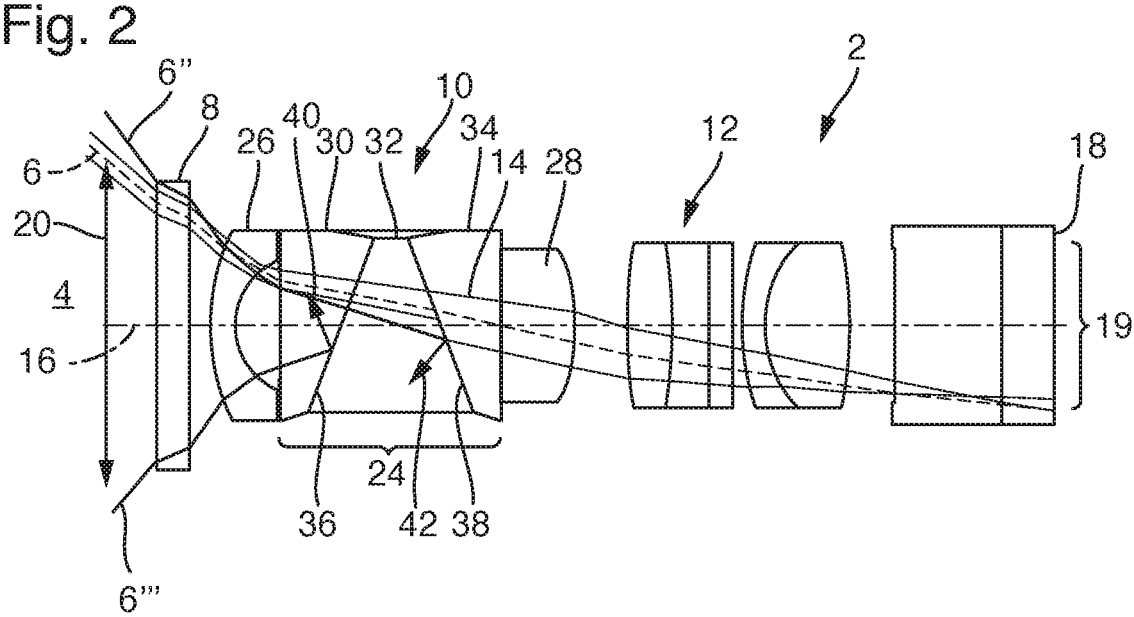
FIG. 2 illustrates an optical system according to one exemplary embodiment, in a schematically simplified longitudinal section.

FIG. 2 shows an optical system 2 according to one exemplary embodiment, also in a simplified and schematic longitudinal section view along a vertical section plane. The optical system 2 comprises a distal optical assembly 10 and a proximal optical assembly 12. The distal optical assembly 10 and the proximal optical assembly 12 define a beam path 14 in the optical system 2. Beams of light 6 (of which only one is shown as an example) from the object space 4 entering the optical system 2 in the field of view 20 are imaged on a light-sensitive surface 19 of the image sensor 18.

The optical system 2 according to the exemplary embodiment depicted comprises a prism group 24 arranged in the beam path 14. The prism group 24 comprises at least one prism 30, 32, 34 and limits the field of view 20 of the optical system 2 on at least one side. Along with the prism group 24, the distal optical assembly 10 also includes an entry lens 26 and an exit lens 28. The at least one prism 30, 32, 34 of the prism group 24 comprises a boundary surface 36, 38 at which the incident beams of light 6" entering the optical system 2 outside the field of view 20 are reflected out of the beam path 14 with total reflection.

The prism group 24 shown in FIG. 2 comprises, for example, a first prism 30, a second prism 32 and a third prism 34. The first prism 30 provides a first boundary surface 36 at which a first light beam 40 (suggested by an arrow) is reflected out of the beam path 14. The second prism 32 provides a second boundary surface 38 at which a second light beam 42 (suggested by an arrow) is reflected out of the beam path 14 in another direction.

The beams of light reflected out of the beam path 14 enter the optical system 2 as light beam 6" and 6'" from outside the field of view 20. In FIG. 2, the incident light beam 6'" on the underside of the optical system 2 from outside the field of view 20 is completely reflected as a first light beam 40 on the first boundary surface 36 and thus removed from the beam path 14. The incident light beam 6" on the upper side of the optical system 2 from outside the field of view 20 is completely reflected as a second light beam 42 on the second boundary surface 38 and reflected out of the beam path 14 in this manner.

The prism group 24 limits the field of view 20 on two mutually opposing sides, for example on a lower and an upper horizontal edge of the field of view 20. Incident beams of light 6", 6'" in the optical system 2, which enter from outside the field of view 20, are reflected out of the beam path 14 on these sides of the field of view 20. In the same way, by rotating the prism group 24 about the optical axis 16, a limitation, for example on the vertical edges of the field of view 20, can result as on the left or right side of the field of view 20. For this, the prism group 24 would have to be rotated by 90° about the optical axis 16; furthermore, it would have to be adapted to the required horizontal viewing angle (which is possibly larger than the vertical viewing angle). Such an adaptation takes place, for example, by a suitable choice of the inclination of the boundary surfaces 36, 38 with respect to the optical axis 16.

It is likewise possible to add a further prism group 24 not depicted in FIG. 2. With such an exemplary embodiment, a first prism group 24 would be arranged like the prism group 24 shown in FIG. 2, and a second prism group would be arranged afterward in the direction of light incident, rotated by 90° about the optical axis 16. Thus, a limitation of the field of view 20 could be achieved on both the horizontal and vertical limits of the field of view 20.

FIG. 3 shows the prism group 24 from FIG. 2, also in a schematically simplified vertical longitudinal section. The prism group 24 is embodied in a mirror-symmetric manner with respect to a sectionally suggested vertical plane 52. The vertical plane 52 stands perpendicular on the optical axis 16. The prisms 30, 32, 34 of the prism group 24 can be straight prisms.

The first prism 30 of the prism group 24 and also the third prism 34 are rectangular prisms. The second prism 32 is an isosceles prism. The first prism 30 includes the first boundary surface 36, at which total reflection takes place. There is a first air gap 46 located between this first boundary surface 36 and an entry surface 44 of the second prism 32. There is a second air gap 50 located between a second boundary surface 38, which is an exit area of the second prism 32, and a further entry surface 48 of the third prism 34. On both the first boundary surface 36 and the second boundary surface 38, in each case a transition occurs from an optically denser medium, namely the material of the first prism 30 or respectively the second prism 32, which is glass for example, to an optically less dense medium, namely the air in the respective air gap 46, 50. The beams of light 40, 42 (cf. FIG. 2) are totally reflected on the first and second boundary surfaces 36, 38.

The prisms 30, 32, 34 are arranged adjacent to one another. Thus, there are no additional optical elements between the prisms 30, 32, 34; the prism group 24 comprises no further optical elements. In particular, the entry surface 44 of the second prism 32 is arranged adjacent to the first boundary surface 36 of the first prism 30. Between these two boundary surfaces 36, 44 is only the first air gap 46. The same applies to the arrangement of the second and third prisms 32, 34. Here too, the additional entry surface 48 of the third prism 34 is arranged adjacent to the second boundary surface 38. Between these two surfaces 38, 48 is only the second air gap 50. According to further exemplary embodiments, it is provided that instead of the air gap 46, 50 the gap be filled with an optically less dense medium. It is critical that the optical density of this medium be lower than the optical density of the material of the first prism 30 in the case of the first air gap 46, and optically less dense than the material of the second prism 32 in the case of the second air gap 50. The prisms 30, 32, 34 can be cemented to one another, for example.

The first boundary surface 36 and the second boundary surface 38 are inclined in different directions. This causes the beams of light 40, 42 reflected out of the beam path 14 to be reflected out from it in different directions. Due to the symmetrical design of the prism group 24, the boundary surfaces 36, 38 are each inclined by the same angle. Furthermore, their inclination is on axes which are parallel to one another.

FIG. 4 shows a further schematic representation of the prism group 24. The first prism 30 comprises two optically effective prism surfaces 54, 54' which enclose an acute angle α. Furthermore, the first prism 30 comprises an optically non-effective surface 56 opposite to the acute angle α. The first optically effective prism surface 54 lies on a first plane E1 (suggested by a dot-dashed line). The second optically effective prism surface 54' lies on a second plane E2. The surface 56 lies on a third plane E3. The first through third planes E1, E2, E3 enclose a triangle which is at least sectionally a base area of the straight first prism 30. The actual base area of the prism 32 is a triangle, the tip of which is truncated. Corresponding designs can be found for the second and third prisms 32, 34. The two respective optically effective prism surfaces likewise enclose an acute angle which lies opposite a further surface of the prism 32, 34 which is not optically effective. These surfaces lie in planes which enclose a triangle which forms the base area of the prism in sections. For example, along with the first prism 30, the prism group 24 includes the second prism 32, which in this sense is also configured like the first prism 30. The second prism 32 also includes the optically effective prism surfaces 54", 54'" which lie opposite a surface 56' and enclose an acute angle β.

The first and second prisms 30, 32 are arranged such that the first acute angle α of the first prism 30 and the second acute angle β of the second prism 32 lie on mutually opposing sides of the prism group 24. The acute angles α, β thus lie opposite one another.

The previously described design principles also apply to the prism group 24 of the exemplary embodiment in FIG. 6, which shall be discussed in detail further below.

Figure 5:
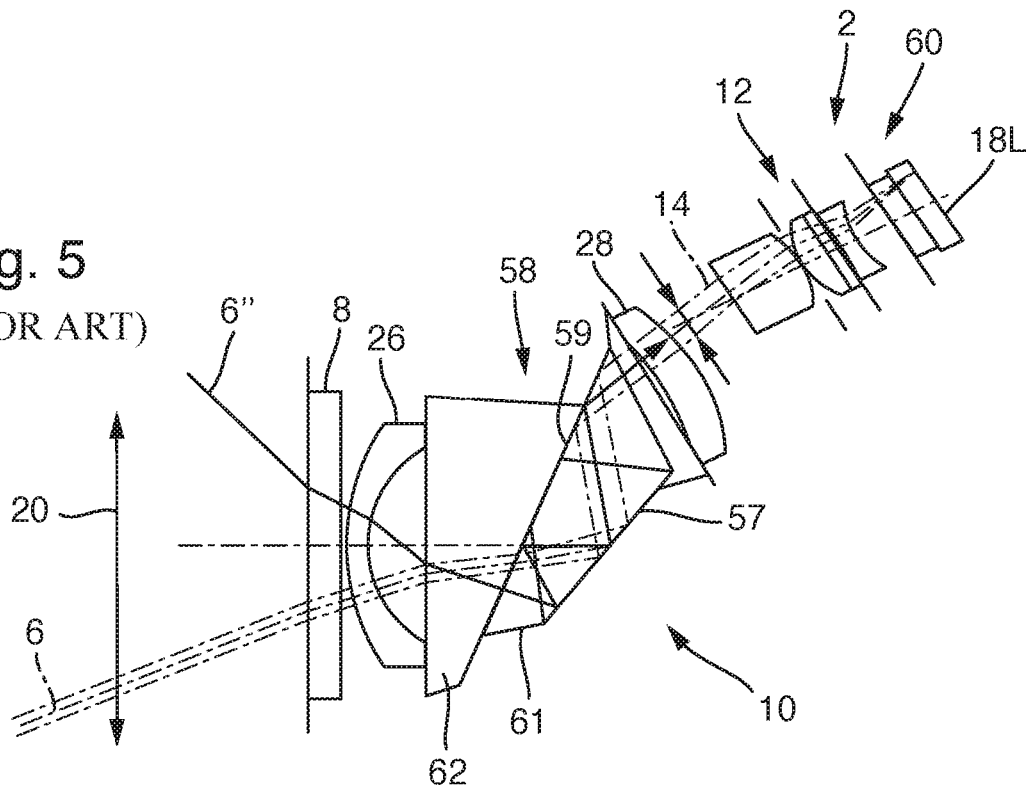
FIG. 5 illustrates a further optical system according to prior art in a schematically simplified longitudinal section, wherein only a left lens system channel of its proximal optical assembly is shown.
Figure 6:
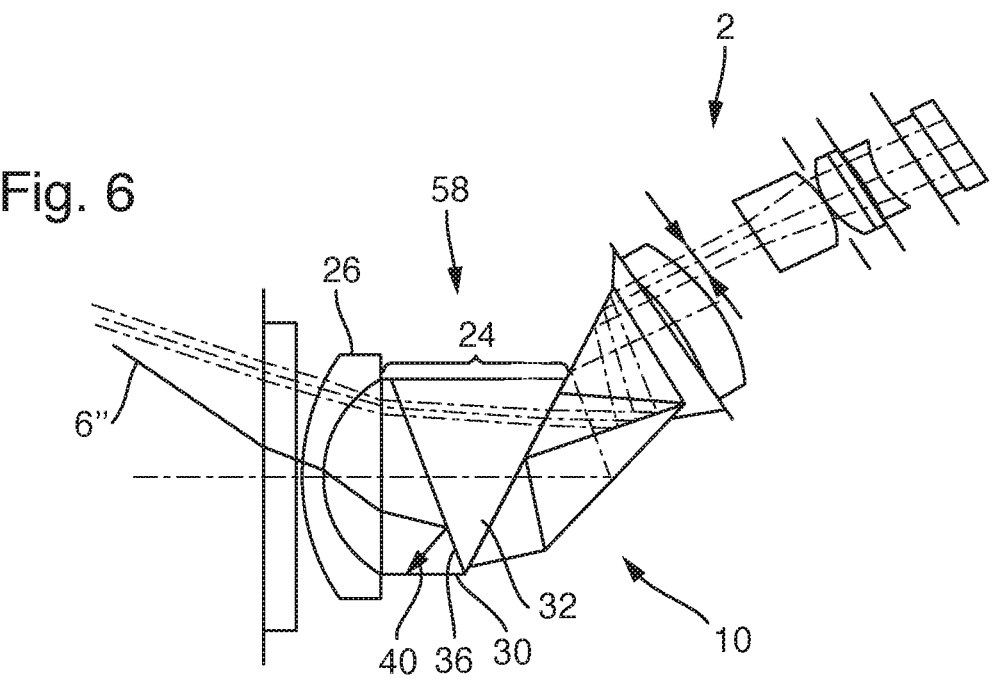
FIG. 6 illustrates an optical system of a stereo video endoscope according to one exemplary embodiment, comprising a prism group, wherein only the left lens system channel of the proximal optical assembly is shown.

FIG. 6 shows another optical system 2 according to one exemplary embodiment. The optical system 2 is, for example, the optical system 2 of a stereo video endoscope. The optical system 2 includes, as part of the deflecting prism group 58, a prism group 24, which includes a boundary surface 36 at which the incident light beam 6" from outside the field of view 20 is reflected out of the beam path 14 as a first light beam 40. The prism group 24 includes the first prism 30 and the second prism 32 for this purpose. Once again, a first air gap can be provided between the first boundary surface 36 of the first prism 30 so that total reflection takes place on the boundary surface 36. The first and second prisms 30, 32 are particularly configured in such a way that these replace the first deflecting prism 62 of the deflecting prism group 58 shown in FIG. 5; i.e. produce an equivalent optical effect (aside from the total reflection of beams of light 6" not coming from the field of view 20).

The arrangement of the prism group 24 can be directly adjacent to the entry lens 26. This applies for the exemplary embodiment in FIG. 2 and in FIG. 6. The prism group 24, which in each case is a part of the distal optical assembly 10, removes undesirable scattered light directly at the beginning of the optical system 2. This increases the imaging quality of the optical system 2.

While there has been shown and described what is considered to be preferred embodiments, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE NUMBERS

2 Optical system
4 Object space
6, 6', 6", 6'" Beams of light
8 Entry window
10 Distal optical assembly
12 Proximal optical assembly
14 Beam path
16 Optical axis
18 Image sensor
19 Light-sensitive surface
20 Field of view
22 Scattering center
24 Prism group
26 Entry lens
28 Exit lens
30 First prism
32 Second prism 34 Third prism
36 First boundary surface
38 Second boundary surface
40 First light beam
42 Second light beam
44 Entry area
46 First air gap
48 Additional entry area
50 Second air gap
52 Vertical plane
54, 54' Optically effective prism surface
56 Surface
57 Back side
58 Deflecting prism group
59 Front side
60 Left lens system channel
61 Second deflecting prism
62 First deflecting prism
E1, E2, E3 Plane

What is claimed is:

1. An optical system comprising:
a distal optical assembly;
a proximal optical assembly; and
an image sensor;
wherein the distal and proximal optical assemblies define a beam path;
the distal optical assembly couples incident beams of light from a field of view located in an object space in the proximal optical assembly;
the proximal optical assembly directs the incident beams of light onto a light-sensitive surface of the image sensor; and
the distal optical assembly comprises, a prism group arranged in the beam path, such that the prism group limits the field of view of the optical system on at least one side, wherein the prism group comprises a first prism and a second prism, wherein
the prism group includes a boundary surface at which the incident beams of light from outside the field of view are reflected out of the beam path, wherein the first prism and the second prism are arranged one after another in a direction of incident light, wherein an air gap is present between the first prism and the second prism and the boundary surface is a surface of the first prism contacting the air gap, and
the second prism is a straight prism having a first optically effective prism surface and a second optically effective prism surface which enclose an acute angle and a third surface opposite the acute angle, wherein the third surface is optically non effective, wherein a first plane in which the first optically effective prism surface lies, a second plane in which the second optically effective prism surface lies, and a third plane in which the third surface lies together enclose a triangle.

2. The optical system according to claim 1, wherein the boundary surface at which the incident beams of light from outside the field of view are reflected out of the beam path with total reflection.

3. The optical system according to claim 2, wherein beams of light reflected out of the beam path enter the distal optical assembly on one side of the field of view, at which the prism group of the field of view is limited.

4. The optical system according to claim 2, wherein total reflection occurs at the boundary surface and the second prism is arranged abutting the air gap.

5. The optical system according to claim 1, wherein the first prism is a rectangular prism.

6. The optical system according to claim 1, wherein the prism group is a part of the distal optical assembly and the distal optical assembly further comprises an entry lens wherein the prism group is arranged directly after the entry lens in the direction of incident light.

* * * * *